United States Patent
Lee et al.

(10) Patent No.: US 9,744,080 B2
(45) Date of Patent: *Aug. 29, 2017

(54) APERTURED POLYMERIC FILM WEBS AND ABSORBENT ARTICLES USING SUCH WEBS

(75) Inventors: Yann-Per Lee, Fairfield, OH (US); Saeed Fereshtehkhou, Cincinnati, OH (US); Keith J. Stone, Fairfield, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 890 days.

This patent is subject to a terminal disclaimer.

(21) Appl. No.: 12/193,325

(22) Filed: Aug. 18, 2008

(65) Prior Publication Data

US 2009/0026651 A1    Jan. 29, 2009

Related U.S. Application Data

(60) Division of application No. 11/130,877, filed on May 17, 2005, which is a continuation of application No.
(Continued)

(51) Int. Cl.
   *B26F 1/26* (2006.01)
   *A61F 13/15* (2006.01)
   (Continued)

(52) U.S. Cl.
   CPC .. *A61F 13/15731* (2013.01); *A61F 13/15203* (2013.01); *A61F 13/512* (2013.01);
   (Continued)

(58) Field of Classification Search
   CPC .......... A61F 13/15731; A61F 13/15203; A61F 13/512; B26F 1/26; B32B 3/10
   (Continued)

(56) References Cited

U.S. PATENT DOCUMENTS

| 4,319,868 A | 3/1982 | Riemersma |
|---|---|---|
| 4,327,730 A | 5/1982 | Sorensen |

(Continued)

FOREIGN PATENT DOCUMENTS

| EP | 0 820 747 A1 | 1/1998 |
|---|---|---|
| EP | 0 955 159 A1 | 11/1999 |

(Continued)

OTHER PUBLICATIONS

Office Action for U.S. Appl. No. 11/130,877 dated Apr. 16, 2008; Lee et al.; filed May 17, 2005.
(Continued)

*Primary Examiner* — Mathieu Vargot
(74) *Attorney, Agent, or Firm* — George H. Leal; Andres Ernesto Velarde; Andrew J. Hagerty

(57) ABSTRACT

A method for making an apertured polymeric film web, the method comprising the steps of:
 a. providing a polymeric film web;
 b. providing a first process selected from the group consisting of, hydroforming, vacuum forming, needle punching, mechanical embossing, flocking, ultrasonics, printed hair, brushing, and combinations thereof;
 c. providing a second process, different from the first process, the second process selected from the group consisting of, hydroforming, vacuum forming, needle punching, mechanical embossing, ultrasonics, stretch rupturing, hydrocutting, hydrosonics, slitting, ring-rolling, and combinations thereof;
 d. forming three dimensional surface structures in the polymeric film web by the first process; and
 e. forming fluid transport apertures in the polymeric film web by the second process.

10 Claims, 4 Drawing Sheets

Related U.S. Application Data

10/217,911, filed on Aug. 13, 2002, now abandoned, which is a division of application No. 09/544,886, filed on Apr. 7, 2000, now abandoned.

(51) Int. Cl.
| | | |
|---|---|---|
| *A61F 13/512* | (2006.01) | |
| *B32B 3/10* | (2006.01) | |
| *A61F 13/511* | (2006.01) | |
| *A61F 13/513* | (2006.01) | |
| *B26F 1/10* | (2006.01) | |
| *B26F 1/24* | (2006.01) | |

(52) U.S. Cl.
CPC .................. *B26F 1/26* (2013.01); *B32B 3/10* (2013.01); *A61F 13/5116* (2013.01); *A61F 2013/1543* (2013.01); *A61F 2013/51165* (2013.01); *A61F 2013/51338* (2013.01); *A61F 2013/51366* (2013.01); *B26F 1/10* (2013.01); *B26F 1/24* (2013.01); *Y10T 428/24273* (2015.01); *Y10T 428/24322* (2015.01); *Y10T 428/249953* (2015.04)

(58) Field of Classification Search
USPC .......................................... 264/1.6, 2.7, 156
See application file for complete search history.

(56) References Cited

U.S. PATENT DOCUMENTS

| | | | |
|---|---|---|---|
| 4,377,544 A | 3/1983 | Rasmussen | |
| 4,395,215 A * | 7/1983 | Bishop | ..................... 425/290 |
| 4,609,518 A | 9/1986 | Baird et al. | |
| 4,614,679 A | 9/1986 | Rattray et al. | |
| 4,629,643 A | 12/1986 | Curro | |
| 4,637,819 A | 1/1987 | Ouellette et al. | |
| 5,188,625 A * | 2/1993 | Van Iten et al. | ............... 604/383 |
| 5,603,707 A | 2/1997 | Trombetta | |
| 5,628,844 A | 5/1997 | Takai et al. | |
| 5,635,275 A | 6/1997 | Biagioli | |
| 5,643,240 A | 7/1997 | Jackson | |
| 5,965,235 A * | 10/1999 | McGuire et al. | ............. 428/156 |
| 5,990,377 A | 11/1999 | Chen et al. | |
| 5,997,986 A | 12/1999 | Turi et al. | |
| 6,025,049 A | 2/2000 | Ouellette et al. | |
| 6,599,612 B1 | 7/2003 | Gray | |
| 2002/0026166 A1 | 2/2002 | Graef et al. | |
| 2003/0003269 A1 | 1/2003 | Lee et al. | |
| 2003/0018311 A1 | 1/2003 | Graef et al. | |
| 2004/0161586 A1 | 8/2004 | Cree | |
| 2005/0214506 A1 | 9/2005 | Lee et al. | |

FOREIGN PATENT DOCUMENTS

| | | | |
|---|---|---|---|
| JP | 11-239587 | * | 9/1999 |
| WO | WO-97/00060 A1 | | 1/1997 |
| WO | WO-98/25759 A1 | | 6/1998 |
| WO | WO 99/55273 A1 | | 11/1999 |
| WO | WO 00/23024 A1 | | 4/2000 |
| WO | WO 02/24133 A1 | | 3/2002 |
| WO | WO 02/098338 A1 | | 12/2002 |

OTHER PUBLICATIONS

Office Action for U.S. Appl. No. 11/130,877 dated Oct. 16, 2008; Lee et al.; filed May 17, 2005.
Examiner's Answer for U.S. Appl. No. 11/130,877 dated May 13, 2009; Lee et al.; filed May 17, 2005.
PCT International Search Report dated Oct. 24, 2001—10 pages.
EPO Search Report dated Dec. 6, 2006—8 pages.

* cited by examiner

APERTURED POLYMERIC FILM WEBS AND ABSORBENT ARTICLES USING SUCH WEBS

CROSS REFERENCE TO RELATED APPLICATION

This application is a divisional of U.S. application Ser. No. 11/130,877, filed on May 17, 2005, which is a continuation of U.S. application Ser. No. 10/217,911 filed Aug. 13, 2002, abandoned, which is a divisional of U.S. application Ser. No. 09/544,886 filed Apr. 7, 2000, abandoned.

FIELD OF THE INVENTION

The present invention relates methods for making an apertured polymeric film web exhibiting a soft and silky tactile impression on at least one of its surfaces. The present invention also relates to absorbent articles incorporating a topsheet comprised of a web according to the present invention.

BACKGROUND OF THE INVENTION

It has long been known in the field of disposable absorbent articles that it is extremely desirable to construct absorptive devices, such as disposable diapers, sanitary napkins, incontinent briefs, bandages, wound dressings, and the like, presenting a soft, silky, cloth-like surface feel to the user to improve wearing comfort and confidence.

One solution to the aforementioned problem has been to utilize a covering or topsheet on the exposed, wearer-contacting layer which comprises a web of formed, apertured thermoplastic film. Commonly assigned U.S. Pat. No. 4,342,314, issued to Radel et al. on Aug. 3, 1982 discloses a representative formed film of this variety. In order to address consumer concerns with regard to plastic-like appearance and feel, webs of this variety have been developed which include an interconnected structure of fiber-like appearance in the interest of generating a more cloth-like, aesthetically-pleasing appearance. In addition, apertured, formed thermoplastic film webs have been developed which further include microscopic surface texturing (microtexture) and/or microscopic apertures (microapertures) to further enhance the visual and tactile impression of such webs. Representative film webs of this variety are disclosed in commonly assigned U.S. Pat. No. 4,463,045, issued to Ahr et al. on Jul. 31, 1984, U.S. Pat. No. 4,629,643, issued Dec. 16, 1986 to Curro et al., and U.S. Pat. No. 4,609,518, issued Sep. 2, 1986 to Curro et al.

Another solution has been to utilize a fibrous material as a covering or topsheet on such articles, alone or as an overlay or laminate over other materials. A representative topsheet structure of this variety is disclosed in Statutory Invention Registration H1670 published in the name of Aziz et al. on Jul. 1, 1997. Such fibrous materials may take the form of a woven or nonwoven web of a suitable fiber variety, and may or may not include discretely formed apertures in addition to the inherent porosity of the web itself. Such fibrous webs exhibit an aesthetically-pleasing, cloth-like surface appearance and tactile impression due to the fibrous nature of the surface.

While fibrous webs tend to have more cloth-like aesthetics than film webs they also tend to retain fluid in the fiber interstices resulting in a wet topsheet versus films. What is needed then is a film-based web that has fibrous web-like aesthetics. The aforementioned Curro et al. patent makes some progress towards this end compared to the aforementioned Radel et al., but does not make a film web nearly as soft as the present invention.

SUMMARY OF THE INVENTION

A method for making an apertured polymeric film web, the method comprising the steps of:
  a. providing a polymeric film web;
  b. providing a first process selected from the group consisting of, hydroforming, vacuum forming, needle punching, mechanical embossing, flocking, ultrasonics, printed hair, brushing, and combinations thereof;
  c. providing a second process, different from the first process, the second process selected from the group consisting of, hydroforming, vacuum forming, needle punching, mechanical embossing, ultrasonics, stretch rupturing, hydrocutting, hydrosonics, slitting, ring-rolling, and combinations thereof;
  d. forming three dimensional surface structures in the polymeric film web by the first process; and
  e. forming fluid transport apertures in the polymeric film web by the second process.

BRIEF DESCRIPTION OF THE DRAWINGS

While the specification concludes with claims particularly pointing out and distinctly claiming the present invention, it is believed that the present invention will be better understood from the following description in conjunction with the accompanying drawings, in which like reference numbers identify like elements, and wherein:

DETAILED DESCRIPTION OF THE PRESENT INVENTION

Definitions

Figure 1:
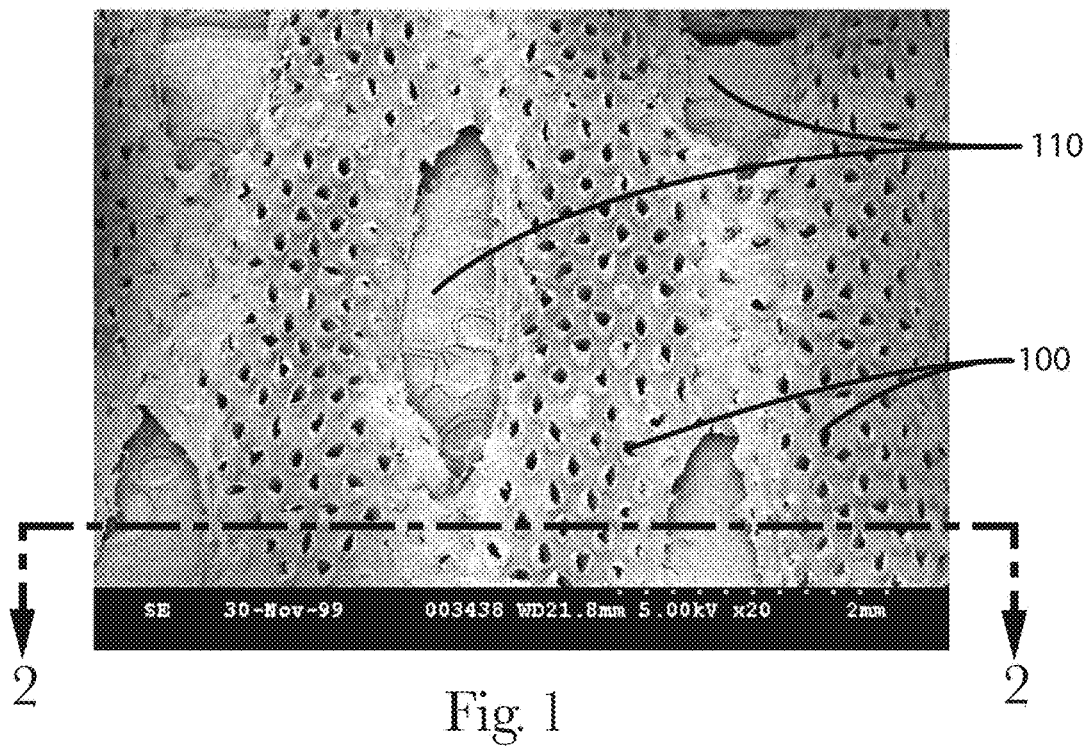
FIG. 1 is a plan view scanning electron micrograph showing one embodiment of thermoplastic web of the present invention.

As used herein, the term "hydrophilic" is used to refer to surfaces that are wettable by aqueous fluids (e.g., aqueous body fluids) deposited thereon. Hydrophilicity and wettability are typically defined in terms of water contact angle and the surface tension of the fluids and solid surfaces involved. This is discussed in detail in the American Chemical Society publication entitled Contact Angle, Wettability and Adhesion, edited by Robert F. Gould (Copyright 1964). A surface is said to be wetted by a fluid (hydrophilic) when the fluid tends to spread spontaneously across the surface as opposed to forming discrete droplets. Conversely, a surface is considered to be "hydrophobic" if the fluid tends to form discrete droplets and does not spread spontaneously across the surface. As used herein, a "hydrophilic web or layer" generally has a water contact angle less than about 50 degrees. As used herein, a "hydrophobic web or layer" generally has a water contact angle greater than about 50 degrees.

The term "permanently hydrophilic" as used herein refers to a web that retains its low contact angle over long periods of time or after exposure to conditions that would otherwise remove surfactants. Such a film can be comprised of a block copolymer of a polyether and another polymer. Such a composition renders the web permanently hydrophilic thereby giving the web durable wettability without the need for surfactant treatment.

The water contact angle depends on surface inhomogeneities (e.g., chemical and physical properties, such as roughness), contamination, chemical/physical treatment of the solid surface, or composition of the solid surface, as well as contamination of the water. The surface energy of the solid also influences the water contact angle. As the surface energy of the solid decreases, the water contact angle increases. As the surface energy of the solid increases, the water contact angle decreases.

As used herein, the term "gradient" when applied to differences in surface energy or work of adhesion is intended to describe a change in surface energy or work of adhesion occurring over a measurable distance. The term "discontinuity" is intended to refer to a type of "gradient" or transition, wherein the change in surface energy occurs over an essentially zero distance. Accordingly, as used herein all "discontinuities" fall within the definition of "gradient".

Also, as used herein the terms "capillary" and "capillarity" are used to refer to passageways, apertures, pores, or spaces within a structure which are capable of fluid transport in accordance with the principles of capillarity generally represented by the Laplace equation (1):

$$\Delta p = 2G(\cos A)/R \quad (1)$$

where:
p is the capillary pressure;
R is the internal radius of the capillary (capillary radius); and
G is the surface tension of the liquid measured in dyne/cm, and
A is the liquid-solid water contact angle measured in degrees.

As noted in Penetration of Fabrics by Emery I. Valko, found in Chapter III of Chem. Aftertreat. Text. (1971), pp. 83-113, for A=90°, the cosine of A is zero and there is no capillary pressure. For A>90°, the cosine of A is negative and the capillary pressure opposes the entry of fluid into the capillary. For A<90° the cosine of A is positive and the capillary pressure permits spontaneous entry of fluid into the capillary. Also, R must be sufficiently small for p to have a meaningful value, since as R increases (larger aperture/capillary structure) the capillary pressure decreases.

As utilized herein, the term "incompatible" represents the lack of miscibility between two materials such that each phase substantially retains its original properties. Example properties include glass transition temperature or melting point. Another characterization of incompatible materials is that the strength of the interface is significantly weaker than the strength of the weakest individual phase (material). Thus, the work of adhesion between the two materials is much lower than the lowest cohesive energy of either material, and the risk of delamination is high.

The term "tie layer" refers to any layer in a web ply that is comprised of material that serves to tie or join two incompatible materials.

The term "topsheet" generally refers to the cover layer, in an absorbent article such as a diaper or catamenial pad, that faces the wearer of the absorbent article. The term "wearer-contacting layer or surface" as used herein refers to the surface of a topsheet or other absorbent article component that is nearest the wearer of the article. The term "garment-facing layer or surface" refers to the surface of a topsheet or other absorbent article component that faces away from the wearer when the component is used in an absorbent article.

The term "Z-dimension" refers to the dimension orthogonal to the length and width of the layer, structure or article. The Z-dimension usually corresponds to the thickness of the layer, structure or article.

The term "three dimensional surface structure" refers to any three dimensional structure residing on the web surface that serves to enhance the soft and silky tactile impression of the web. Examples of such structures include but are not limited to the following: aberrations; fibrils; incongruities; cone structures; and apertures. Methods for providing three dimensional surface structures can be broken into two groups: 1) apertured methods; and 2) non-apertured methods.

Apertured methods include but are not limited to the following: vacuum forming, hydroforming, needle punching (solid or hollow), hydrosonics, ultrasonics, and any combination thereof.

Non-apertured methods include but are not limited to the following: mechanical embossing, flocking, delamination of viscous melts or optionally delamination of viscous melts from porous surfaces, printed hair, brushing, and any combination thereof.

The term "fluid transport aperture" refers to any aperture in the web that serves to transport fluids within the web. Examples of fluid transport aperturing processes include but are not limited to the following: mechanical embossing; stretch rupturing; vacuum forming; hydroforming; hydrocutting; needle punching (solid or hollow); hydrosonics; ultrasonics; slitting; ring-rolling; structural elastic-like web; and any combination thereof.

As utilized herein, the term "fluid passageway" is intended to encompass enclosed or at least partially enclosed structures or channels which may communicate fluids. The term fluid passageway is thus intended to encompass the terms "aperture", "channel", "capillary", as well as other similar terms. The passageways inherent in fluid permeable materials are another example. Many other examples of fluid passageways exist in the art and may be used in the present invention.

The term "monolayer" refers to a ply that is comprised of a single layer of material.

The term "sub-ply" refers to a ply located beneath the body contacting ply.

The term "web" as used herein refers to a structure comprised of one or more ply.

The term "layer" as used herein refers to an individual layer or layers of material that are joined to form a ply.

The term "ply" as used herein refers to a structure that is comprised of one or more layers of material.

The term "surface" as used herein refers to a top or first side of a layer and/or a bottom or second side of a layer.

As used herein, the term "absorbent article" refers to devices which absorb and contain body exudates, and, more specifically, refers to devices which are placed against or in proximity to the body of the wearer to absorb and contain the various exudates discharged from the body. The term "disposable" is used herein to describe absorbent articles which are not intended to be laundered or otherwise restored or reused as an absorbent article (i.e., they are intended to be discarded after a single use, and, preferably, to be recycled, composted or otherwise disposed of in an environmentally compatible manner). A "unitary" absorbent article refers to absorbent articles which are formed of separate parts united together to form a coordinated entity so that they do not require separate manipulative parts like a separate holder and pad.

The Apertured Polymeric Web of the Present Invention

The apertured polymeric film web of the present invention is a web material that has been (1) provided with a multiplicity of substantially three dimensional surface structures that cause the web material to exhibit a soft, silky surface to improve the wearer's comfort and (2) provided with fluid transport apertures for improved fluid handling.

Figure 2:
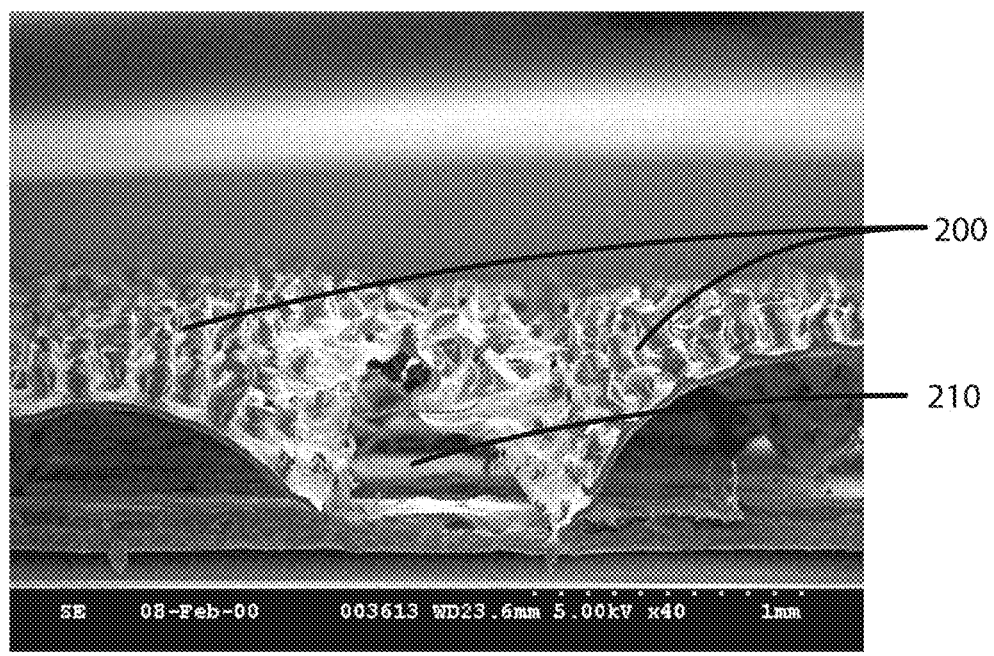
FIG. 2 is an enlarged cross-sectional scanning electron micrograph showing an arrangement of three dimensional surface structures and fluid transport apertures according to the present invention.

FIG. 1 is a plan view scanning electron micrograph of one embodiment of the formed web and depicts the three dimensional surface structures 100 and the fluid transport apertures 110 of the present invention web. FIG. 2 depicts an enlarged cross-sectional scanning electron micrograph along line A-A of FIG. 1 that shows the dimensional relationship of the three dimensional surface structures 100 and fluid transport apertures 110 according to the present invention. The size of both the three dimensional surface structures 100 and fluid transport apertures 110 may be varied. However, in a preferred embodiment the three dimensional surface structures are comprised of microapertures having a diameter of about 0.02-0.2 mm, a height of about 0.02-0.2 mm, and fluid transport apertures having a minimum diameter of about 0.05 mm. As is well known in the art, smaller fluid transport apertures will require apertures comprised of more hydrophilic materials to ensure sufficient fluid management properties.

Figure 3:
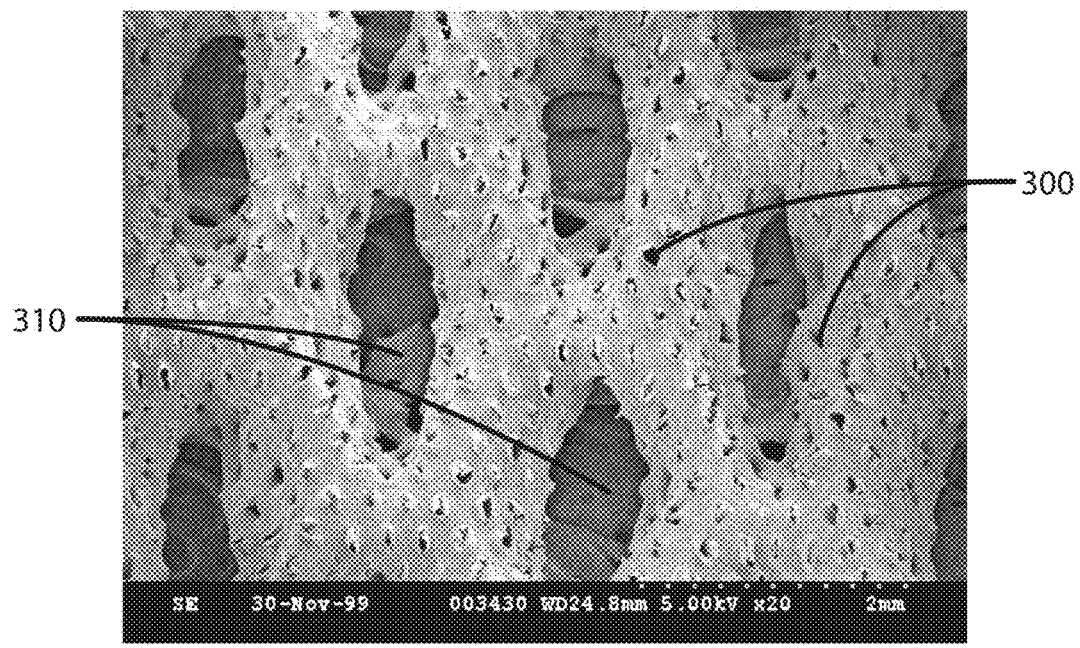
FIG. 3 is a plan view scanning electron micrograph that shows a web manufactured in a double hydroforming process as known in the prior art.
Figure 4:
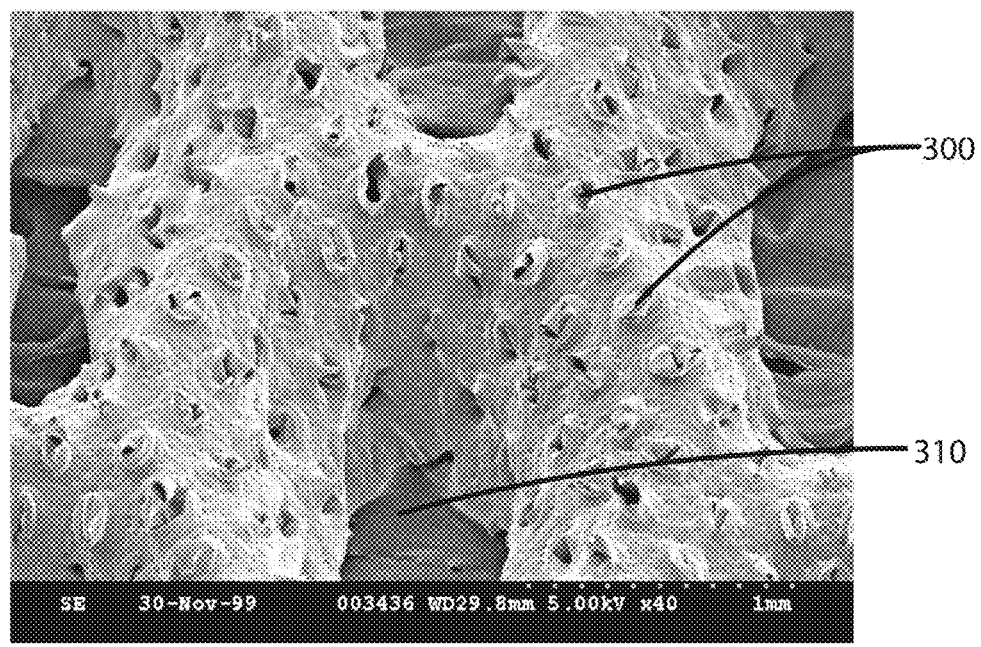
FIG. 4 is a tilt view scanning electron micrograph that shows a web manufactured in a double hydroforming process as known in the prior art.
Figure 5:
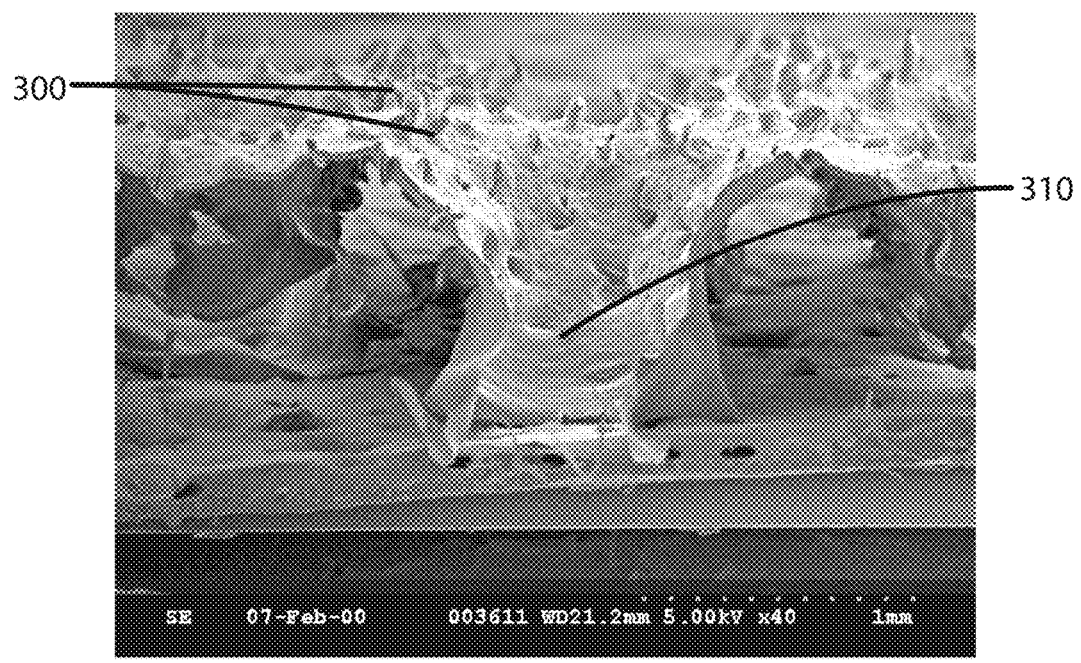
FIG. 5 is a cross-sectional view scanning electron micrograph that shows a web manufactured in a double hydroforming process as known in the prior art.
Figure 6:
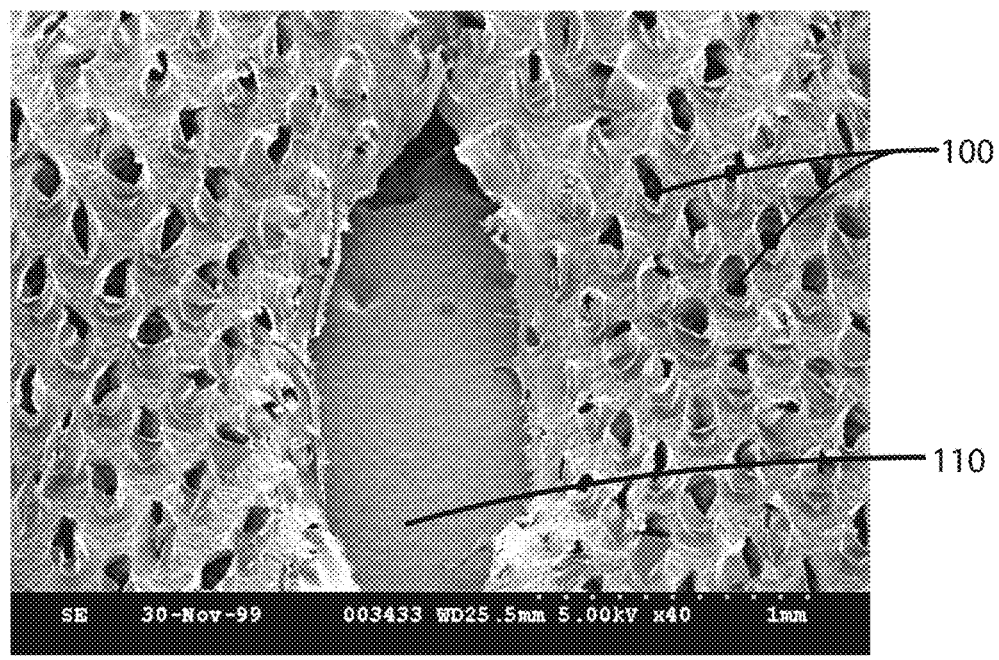
FIG. 6 is a cross-sectional view scanning electron micrograph that shows a web according to the present invention.

FIGS. 3-5 are enlarged scanning electron micrograph depicting the plan view, tilt view, and cross section view of a typical prior art web wherein both three dimensional surface structures 300 and fluid transport apertures 310 were developed using hydroforming processes. A comparison of these scanning electron micrographs reveals that the three dimensional surface structures 110 of the present invention as depicted in FIG. 1 are substantially less damaged than the three dimensional surface structures 310 developed by the double-hydroforming processes.

One aspect of the present invention is a fluid pervious web suitable for use as a topsheet in an absorbent article. In a preferred embodiment, the fluid pervious web of the present invention contains a plurality of microapertures. Although the fluid pervious web of the present invention is described herein as a topsheet for use in an absorbent article, one having ordinary skill in the art would recognize that the fluid pervious web of the present invention would have other uses, such as bandages, agricultural coverings, and similar uses where it is desirable to manage fluid flow through a web or ply.

Providing the fluid pervious web with fluid transport apertures provides the fluid handling properties of the web. In a preferred embodiment of the present invention, fluid transport apertures 110 are provided to the web using means that leave the three dimensional surface structures 100 substantially unaltered relative to their as-made state. In a preferred embodiment of the present invention, fluid transport apertures 110 are provided by mechanically embossing and stretch rupturing the web as discussed below.

Web Material Characteristics

As described herein above, another aspect of the present invention is a topsheet comprising the polymeric film web of the present invention. The material selected for the polymeric film web of the present invention, and therefore for the topsheet formed there from, is preferably machinable and capable of being formed into a sheet. Since the topsheet is to be used in consumer products which contact the human body, the material utilized in the polymeric film web and used to form the topsheet is safe for epidermal or other human contact.

Examples of acceptable web materials are disclosed in commonly assigned U.S. Pat. No. 4,463,045, issued to Ahr, et al. on Jul. 31, 1984, and U.S. Pat. No. 4,629,643, issued Dec. 16, 1986 to Curro et al.

In one embodiment of the present invention, the web material selected creates a surface energy gradient between at least two of the web surfaces. Whenever the wearer-contacting layer and the garment-facing layer of the topsheet of the present invention comprise materials having different layer properties (e.g., one of the layers is hydrophobic and the other is hydrophilic), a surface energy gradient is created. Surface energy gradients have been found to be useful in promoting fluid transport. A comprehensive explanation of surface energy gradients is described in pending U.S. application Ser. No. 09/344,161, U.S. Pat. No. 6,461,716, issued to Lee, et al. on Oct. 8, 2002. In one embodiment of the present invention, the web material used is comprised of hydrophobic and permanently hydrophilic layers, as described in U.S. Pat. No. 6,461,716 to Lee, et al.

The performance properties of the topsheet of the present invention may be manipulated depending on the orientation of the hydrophilic layer and the hydrophobic layer in the thermoplastic formed web ply from which the topsheet is formed. As described above, the thermoplastic formed web ply of the present invention may comprise any number of layers. The topsheet may be formed so that the wearer-contacting layer is a hydrophobic layer and the garment-facing layer is hydrophilic (known as "phobic/philic"), or so that the wearer-contacting layer is hydrophilic and the garment facing layer is hydrophobic (known as "philic/phobic"). In addition, by varying both the orientation of the hydrophilic and hydrophobic layers, many different topsheet structures, with different advantageous properties, can be formed according to the present invention.

The Multi-Ply Composite Structure of the Present Invention

As described above, the highly compressible webs of the present invention enhance the soft and silky tactile impression when used as topsheets. However, a consequence of these highly compressible materials is that the void volume between the topsheet material and the adjacent material is easily lost under in-use pressures. This can have the negative consequence of poor fluid management. Therefore, by combining the webs of the present invention described above with a sub-ply that is relatively non-compressible, the void volume can be protected and serve to provide better fluid management.

Figure 7:
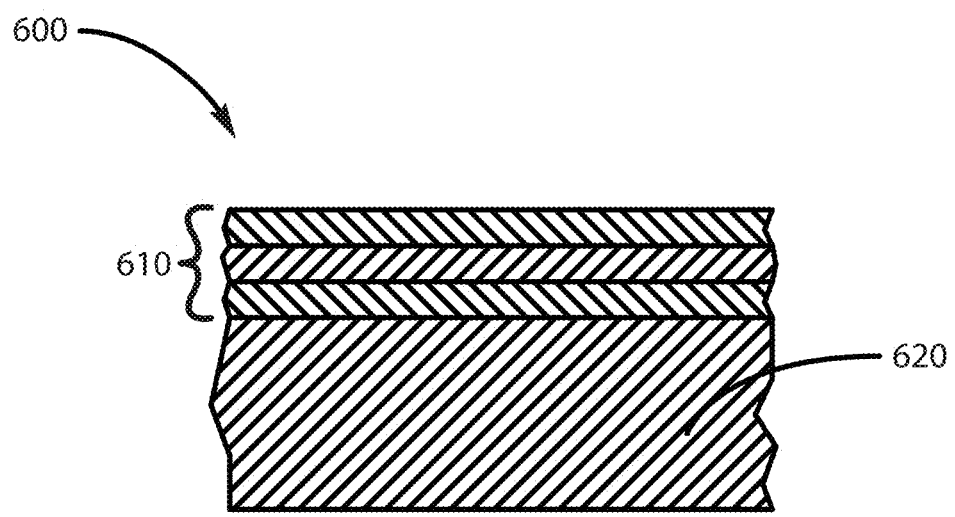
FIG. 7 is a cross-sectional representation of a multi-ply web of the present invention.

An alternative topsheet orientation, shown in FIG. 7, includes a thermoplastic formed film ply 610 comprised of polymeric film web material exhibiting preferred softness and/or compressibility and a sub-ply 620 to form a multi-ply composite structure 600.

The multi-ply composite structure 600 may be formed utilizing various combinations of non-apertured and apertured materials with varying degrees of permeability so long as the multi-ply composite structure 600 serves to transport fluids through the structure. In addition, the materials comprising the multi-ply composite structure 600 may be selected such that a surface energy gradient is formed between at least two exterior surfaces of the structure. In a preferred embodiment of the structure, both ply are provided with fluid transport apertures that form fluid pathways common to both ply. In another embodiment, the multi-ply composite structure 600 is formed such that it maintains a protected void volume during use.

The sub-ply can be comprised of a variety of different materials or combinations thereof. Suitable sub-ply materials include 1) apertured formed webs 2) cloth-like formed webs; 3) nonwovens; 4) wovens; 5) foams; 6) cellulosic webs; and 7) combinations thereof.

Suitable sub-ply formed films are described in U.S. Pat. No. 3,929,135, issued to Thompson on Dec. 30, 1975; U.S. Pat. No. 4,324,246, issued to Mullane, et al. on Apr. 13, 1982; U.S. Pat. No. 4,342,314, issued to Radel, et al. on Aug. 3, 1982; U.S. Pat. No. 4,463,045, issued to Ahr, et al. on Jul. 31, 1984; and U.S. Pat. No. 5,006,394, issued to Baird on Apr. 9, 1991. One especially preferred formed web is described in one or more of the above patents and marketed on sanitary napkins by the Procter & Gamble Company of Cincinnati, Ohio as "DRI-WEAVE".

Alternatively, cloth-like formed films may comprise the sub-ply. Such webs have a softer, more cloth-like feel. Cloth-like formed webs are developed by providing the web surface with either microapertures (as described above), surface texture (described below), or surface treatment (described below), or a combination thereof. The sub-ply may also be comprised of any nonwoven or woven material capable of transporting blood, menses, and/or urine. Other materials not listed herein, but capable of transporting blood, menses, and/or urine, are included in the present invention.

The thermoplastic formed web ply of the present invention may include any number of layers as long as there is a tie layer between any adjacent layers that comprise incompatible materials. In addition, the intermediate layer or layers may comprise any thermoplastic material as long as there is a tie layer between any adjacent incompatible layers. Any number of intermediate layers may be utilized in forming the thermoplastic formed web plies of the present invention.

Methods of Making

The polymeric film web of the present invention may be processed using conventional procedures for producing multi-layer webs on conventional coextruded web-making equipment. In general, polymers can be melt processed into webs using either cast or blown web extrusion methods both of which are described in Plastics Extrusion Technology—2nd Ed., by Allan A. Griff (Van Nostrand Reinhold—1976). A cast web is extruded through a linear slot die. Generally, the flat web is cooled on a large moving polished metal roll (chill roll). It quickly cools, and peels off the first roll, passes over one or more auxiliary rolls, then through a set of rubber-coated pull or "haul-off" rolls, and finally to a winder.

In blown web extrusion the melt is extruded upward through a thin annular die opening. This process is also referred to as tubular web extrusion. Air is introduced through the center of the die to inflate the tube and causes it to expand. A moving bubble is thus formed which is held at constant size by simultaneous control of internal air pressure, extrusion rate, and haul-off speed. The tube of web is cooled by air blown through one or more chill rings surrounding the tube. The tube is next collapsed by drawing it into a flattened frame through a pair of pull rolls and into a winder.

A coextrusion process requires more than one extruder and either a coextrusion feedblock or a multi-manifold die system or combination of the two to achieve the multilayer web structure. U.S. Pat. Nos. 4,152,387 and 4,197,069, issued May 1, 1979 and Apr. 8, 1980, respectively, both to Cloeren, disclose the feedblock and multi-manifold die principle of coextrusion. Multiple extruders are connected to the feedblock which can employ moveable flow dividers to proportionally change the geometry of each individual flow channel in direct relation to the volume of polymer passing through the flow channels. The flow channels are designed such that, at their point of confluence, the materials flow together at the same velocities and pressure, minimizing interfacial stress and flow instabilities. Once the materials are joined in the feedblock, they flow into a single manifold die as a composite structure. Other examples of feedblock and die systems are disclosed in Extrusion Dies for Plastics and Rubber, W. Michaeli, Hanser, New York, $2^{nd}$ Ed., 1992. It may be important in such processes that the melt viscosities, normal stress differences, and melt temperatures of the material do not differ too greatly. Otherwise, layer encapsulation or flow instabilities may result in the die leading to poor control of layer thickness distribution and defects from non-planar interfaces (e.g. fish eye) in the multilayer web.

An alternative to feedblock coextrusion is a multi-manifold or vane die as disclosed in aforementioned U.S. Pat. Nos. 4,152,387 and 4,197,069, as well as U.S. Pat. No. 4,533,308, issued Aug. 6, 1985 to Cloeren. Whereas in the feedblock system melt streams are brought together outside and prior to entering the die body, in a multi-manifold or vane die each melt stream has its own manifold in the die where the polymers spread independently in their respective manifolds. The melt streams are married near the die exit with each melt stream at full die width. Moveable vanes provide adjustability of the exit of each flow channel in direct proportion to the volume of material flowing through it, allowing the melts to flow together at the same velocity, pressure, and desired width.

Since the melt flow properties and melt temperatures of polymers vary widely, use of a vane die has several advantages. The die lends itself toward thermal isolation characteristics wherein polymers of greatly differing melt temperatures, for example up to 175° F. (80° C.), can be processed together.

Each manifold in a vane die can be designed and tailored to a specific polymer. Thus the flow of each polymer is influenced only by the design of its manifold, and not forces imposed by other polymers. This allows materials with greatly differing melt viscosities to be coextruded into multi-layer webs. In addition, the vane die also provides the ability to tailor the width of individual manifolds, such that an internal layer can be completely surrounded by the outer layer leaving no exposed edges. The aforementioned patents also disclose the combined use of feedblock systems and vane dies to achieve more complex multilayer structures.

One of skill in the art will recognize that the size of an extruder used to produce the webs of the present invention depends on the desired production rate and that several sizes of extruders may be used. Suitable examples include extruders having a 1 (2.5 cm) to 1.5 inch (3.7 cm) diameter with a length/diameter ratio of 24 or 30. If required by greater production demands, the extruder diameter can range upwards. For example, extruders having a diameter between about 2.5 inches (6.4 cm) and about 4 inches (10 cm) can be used to produce the webs of the present invention. A general purpose screw may be used. A suitable feedblock is a single temperature zone, fixed plate block. The distribution plate is machined to provide specific layer thicknesses. For example, for a three layer web, the plate provides layers in an 80/10/10 thickness arrangement, a suitable die is a single temperature zone flat die with "flex-lip" die gap adjustment. The die gap is typically adjusted to be less than 0.020 inches (0.5 mm) and each segment is adjusted to provide for uniform thickness across the web. Any size die may be used as production needs may require, however, 10-14 inch (25-35 cm) dies have been found to be suitable. The chill roll is typically water-cooled. Edge pinning is generally used and occasionally an air knife may be employed.

For some coextruded webs, the placement of a tacky hydrophilic material onto the chill roll may be necessary. When the arrangement places the tacky material onto the chill roll, release paper may be fed between the die and the chill roll to minimize contact of the tacky material with the rolls. However, a preferred arrangement is to extrude the tacky material on the side away from the chill roll. This arrangement generally avoids sticking material onto the chill roll. An extra stripping roll placed above the chill roll may also assist the removal of tacky material and also can provide for additional residence time on the chill roll to assist cooling the web.

Occasionally, tacky material may stick to downstream rolls. This problem may be minimized by either placing a low layer energy (e.g. Teflon®) sleeve on the affected rolls, wrapping Teflon tape on the effected rolls, or by feeding release paper in front of the effected rolls. Finally, if it appears that the tacky material may block to itself on the wound roll, release paper may be added immediately prior to winding. This is a standard method of preventing blocking of web during storage on wound rolls. Processing aids, release agents or contaminants should be minimized. In some cases, these additives can bloom to the layer and reduce the layer energy (raise the contact angle) of the hydrophilic layer.

An alternative method of making the multi-layer webs of the present invention is to extrude a web comprising a material suitable for one of the individual layers. Extrusion methods as may be known to the art for forming flat webs are suitable. Such webs may then be laminated to form a multi-layer web suitable for formation into a fluid pervious web using the methods discussed below. As will be recognized, a suitable material, such as a hot melt adhesive, can be used to join the webs to form the multi-layer web. A preferred adhesive is a pressure sensitive hot melt adhesive such as a linear styrene isoprene styrene ("SIS") hotmelt adhesive, but it is anticipated that other adhesives, such as polyester of polyamide powdered adhesives, hotmelt adhesives with a compatibilizer such as polyester, polyamide or low residual monomer polyurethanes, other hotmelt adhesives, or other pressure sensitive adhesives could be utilized in making the multi-layer webs of the present invention. Alternative methods of joining the webs to form the multi-layer web include, but are not limited to, ultrasonic bonding, thermal bonding, or any other suitable means as are known in the art.

In another alternative method of making the multi-layer formed web plies of the present invention, a base or carrier web can be separately extruded and one or more layers can be extruded thereon using an extrusion coating process to form a multi-layer formed web ply according to the present invention. Preferably, the carrier web passes under an extrusion die at a speed that is coordinated with the extruder speed so as to form a very thin web having a thickness of less than about 25 microns. The molten polymer and the carrier web are brought into intimate contact as the molten polymer cools and bonds with the carrier web. As noted above, a tie layer may enhance bonding between the layers. A tie layer is typically comprised of a thermoplastic material that is able to bond with both adjacent layers. Tie layers are joined to adjacent layers using bonding means including, but not limited to, chemical bonds, physical entanglement of thermoplastic chains, and combinations thereof. Contact and bonding are also normally enhanced by passing the layers through a nip formed between two rolls. The bonding may be further enhanced by subjecting the layer of the carrier web that is to contact the web to layer treatment, such as corona treatment, as is known in the art.

The thermoplastic formed web can be provided with substantially three dimensional surface structures 100 using any process known in the art. Providing the web with three dimensional surface structures will provide the exterior surfaces of the web with a softer, more cloth-like texture, provide the web with a more cloth-like appearance, and increase the overall caliper of the web. Examples of three dimensional surface structures processes include but are not limited to the following: hydroforming, vacuum forming, needle punching (solid or hollow), mechanical embossing, flocking, ultrasonics, delamination of viscous melts from porous surfaces, printed hair, brushing, and any combination thereof.

In a preferred embodiment, three dimensional surface structures 100 comprising microapertures are formed by applying a high pressure fluid jet comprised of water or the like against one surface of the formed web ply, preferably while applying a vacuum adjacent the opposite surface of the formed web ply. In general, the formed web ply is supported on one layer of a forming structure having opposed layers. The forming structure is provided with a multiplicity of apertures there through which place the opposed layers in fluid communication with one another. While the forming structure may be stationary or moving, a preferred embodiment uses the forming structure as part of a continuous process where the formed web ply has a direction of travel and the forming structure carries formed web ply in the direction of travel while supporting the web. The fluid jet and, preferably, the vacuum cooperate to provide a fluid pressure differential across the thickness of the web causing the web to be urged into conformity with the forming structure and to rupture in areas that coincide with the apertures in the forming structure.

Such methods of aperturing are known as "hydroformation" and are described in greater detail in commonly assigned U.S. Pat. No. 4,609,518 issued to Curro, et al. on Sep. 2, 1986; U.S. Pat. No. 4,629,643 issued to Curro, et al. on Dec. 16, 1986; U.S. Pat. No. 4,637,819 issued to Ouellette, et al. on Jan. 20, 1987; U.S. Pat. No. 4,681,793 issued to Linman, et al. on Jul. 21, 1987; U.S. Pat. No. 4,695,422 issued to Curro, et al. on Sep. 22, 1987; U.S. Pat. No. 4,778,644 issued to Curro, et al. on Oct. 18, 1988; U.S. Pat. No. 4,839,216 issued to Curro, et al. on Jun. 13, 1989; and U.S. Pat. No. 4,846,821 issued to Lyons, et al. on Jul. 11, 1989.

As mentioned above, the surface treated web of the present invention may also be formed by methods such as vacuum formation, mechanical methods such as punching, mechanical embossing, flocking, hydrosonics, ultrasonics, delamination of viscous melts or optionally delamination of viscous melts from porous surfaces, printed hair, and brushing.

Vacuum formation is disclosed in U.S. Pat. No. 4,463, 045, issued to Ahr, et al. on Jul. 31, 1984. As disclosed in Ahr et al., micro-textures, i.e., microscopic patterns of surface aberrations to produce three dimensional surface structures 100, can be produced by extruding a resinous melt directly onto the surface of a debossing/perforating cylinder having a microscopic pattern of surface aberrations about its periphery.

Examples of mechanical methods are disclosed in U.S. Pat. No. 4,798,604, issued to Carter on Jan. 17, 1989, U.S. Pat. No. 4,780,352, issued to Palumbo on Oct. 25, 1988, U.S. Pat. No. 3,566,726, issued to Politis on Mar. 2, 1971, U.S. Pat. No. 4,634,440, issued to Widlund, et al. on Jan. 6, 1987, PCT Publication WO 97/40793, issued to Johansson, et al. on Nov. 6, 1997, and European Patent 525,676, issued to Dabi, et al. Johansson, et al., for example, teaches the use of heated needles to penetrate a textile material layer comprising at least one thermoplastic component. Widlund, et. al., also teaches heatable pins on a punch wheel having a shape which conforms to that of the "capillary ducts" as Widlund refers to film apertures.

Examples of mechanical embossing are disclosed in European Patents 862,904, issued to Hisashi, et al. on Sep. 9, 1998, 858,792, issued to Tsuji, et al. on Aug. 19, 1998, Japanese Patents 8-260,329, issued to Wataru, et al., 10-131, 014, issued to Wataru, et al., and U.S. Pat. No. 5,916,661, issued to Benson, et al. on Jun. 29, 1999, U.S. Pat. No. 5,628,097, issued to Benson, et al. on May 13, 1997. Tsuji, et al., for example, disclose an apparatus having a pair of first and second rolls arranged in parallel to each other so as to engage each other and thereby to emboss the web to form liquid passages.

Examples of flocking are disclosed in PCT Publications WO 98/42289, issued to Chen, et al. on Oct. 1, 1998, WO 98/36721, issued to Johansson, et al. on Aug. 27, 1998, and European Patent 861,646, issued to Takai, et al. on Sep. 2, 1998.

Examples of ultrasonics are disclosed in U.S. Pat. No. 5,269,981, issued to Jameson, et al. on Dec. 14, 1993.

Examples of delamination of viscous melts are disclosed in U.S. Pat. No. 3,967,623, issued to Butterworth et al. on Jul. 6, 1976. Examples of delamination of viscous melts from porous surfaces are disclosed in PCT Publication WO 99/06623, issued to Calhoun, et al. on Feb. 11, 1999.

Examples of printed hair are disclosed in U.S. Pat. No. 5,670,110, issued to Dirk, et al. on Sep. 23, 1997.

Examples of brushing are disclosed in PCT Publication WO 99/06623, issued to Calhoun, et al. on Feb. 11, 1999.

The polymeric film web can be provided with fluid transport apertures 110 using any processes known in the art. Aperturing the web will increase the fluid handling properties of the web and provide the web with a more cloth-like, fiber-like appearance. Examples of such processes include but are not limited to the following: mechanical embossing, stretch rupturing, vacuum forming, hydroforming, hydrocutting, needle punching (solid or hollow), ultrasonics, slitting, ring-rolling, structural elastic-like web, and any combination thereof.

In a preferred embodiment, the fluid transport apertures are provided to the web by mechanically embossing and stretch rupturing the web material. Examples of mechanical embossing are disclosed above. Examples of stretch rupturing are disclosed in PCT Publication WO 97/31601, issued to Hansson on Sep. 4, 1997, and the Benson patents listed above.

Methods for vacuum formation, hydroforming, needle punching, and ultrasonics are described above. With respect to ultrasonics, additional methods are disclosed in U.S. Pat. No. 5,879,494, issued to Hoff, et al. on Mar. 9, 1999, U.S. Pat. No. 5,269,981, issued to Jameson, et al. on Dec. 14, 1993, and European Patent 5,355,579, issued to Jameson, et al. on Apr. 7, 1993.

Methods of hydrocutting are disclosed in U.S. Pat. No. 5,567,736, issued to Turi, et al. on Oct. 22, 1996, and U.S. Pat. No. 5,770,144, issued to James, et al. on Jun. 23, 1998.

Suitable slitting methods are disclosed in PCT Publication WO 97/31601, issued to Hansson on Sep. 4, 1997.

Suitable processes for ring rolling or "pre-corrugating" are described in U.S. Pat. No. 4,107,364 issued to Sisson on Aug. 15, 1978, U.S. Pat. No. 4,834,741 issued to Sabee on May 30, 1989, U.S. Pat. No. 5,167,897 issued to Weber et al. on Dec. 1, 1992, U.S. Pat. No. 5,156,793 issued to Buell et al. on Oct. 20, 1992, and U.S. Pat. No. 5,143,679 issued to Weber on Sep. 1, 1992.

Suitable methods of SELF-ing are described in U.S. Pat. No. 5,518,801 issued to Chappell et al. on May 21, 1996.

Absorbent Articles According to the Present Invention

As used herein, the term "absorbent article" refers to devices which absorb and contain body exudates, and, more specifically, refers to devices which are placed against or in proximity to the body of the wearer to absorb and contain the various exudates discharged from the body. The term "disposable" is used herein to describe absorbent articles which are not intended to be laundered or otherwise restored or reused as an absorbent article (i.e., they are intended to be discarded after a single use, and, preferably, to be recycled, composted or otherwise disposed of in an environmentally compatible manner). A "unitary" absorbent article refers to absorbent articles which are formed of separate parts united together to form a coordinated entity so that they do not require separate manipulative parts like a separate holder and pad. Examples of absorbent articles that incorporate the apertured polymeric film web and the multi-ply composite structure of the present invention include disposable articles including sanitary napkins, pantiliners, and diapers as described in the aforementioned U.S. Pat. No. 6,461,716.

All documents cited in the Detailed Description of the Invention are, in relevant part, incorporated herein by reference; the citation of any document is not to be construed as an admission that it is prior art with respect to the present invention. To the extent that any meaning or definition of a term in this written document conflicts with any meaning or definition of the term in a document incorporated by reference, the meaning or definition assigned to the term in this written document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method for making an apertured polymeric film-based web having a first side and a second side, said method comprising the steps of:
   a. providing a first process of vacuum forming, said first process comprising providing a debossing/perforating cylinder comprising a pattern of surface aberrations about its periphery;
   b. extruding a resinous melt onto the surface of said debossing/perforating cylinder;
   c. applying vacuum to the first side of the film-based web from within said debossing/perforating cylinder so as to form a polymeric film-based web comprising three dimensional surface structures in the form of apertured surface structures;

d. providing a second process that is distinct from said first process, said second process comprising providing a pair of first and second rolls arranged so as to engage each other, at least one of said pair of first and second rolls comprising heated needles or heated pins; and e. forming fluid transport apertures in said polymeric film-based web by applying the heated needles or heated pins of said second process to the first side of the film-based web, wherein said apertured surface structures on the first side are substantially maintained by conducting step (e).

2. The method of claim 1, wherein the fluid transport apertures are generally elliptical in shape.

3. The method of claim 1, wherein the fluid transport apertures are non-angular in shape.

4. The method of claim 1, wherein land regions are formed between fluid transport apertures by conducting step (e), wherein the land regions are wider than the adjacent fluid transport apertures.

5. The method of claim 1, wherein the fluid transport apertures comprise diameters of at least about 0.05 mm.

6. The method of claim 1, wherein the three dimensional apertured surface structures comprise diameters of about 0.02 mm to about 0.2 mm.

7. The method of claim 1, wherein the three dimensional apertured surface structures comprise open areas of about 0.003 mm$^2$ to about 0.03 mm$^2$.

8. The method of claim 1, wherein the three dimensional apertured surface structures comprise heights of about 0.02 mm to about 0.2 mm.

9. The method of claim 1, wherein the three dimensional apertured surface structures comprise heights of 0.02 mm to less than 0.1 mm.

10. The method of claim 4, wherein a plurality apertured surface structures are disposed between adjacent fluid transport apertures.

* * * * *